United States Patent [19]

Corasanti

[11] 4,029,086
[45] June 14, 1977

[54] ELECTRODE ARRANGEMENT

[75] Inventor: Eugene R. Corasanti, New Hartford, N.Y.

[73] Assignee: Consolidated Medical Equipment, Inc., Utica, N.Y.

[22] Filed: Aug. 11, 1975

[21] Appl. No.: 603,505

[52] U.S. Cl. .................. 128/2.06 E; 128/2.1 E; 128/417; 128/DIG. 4

[51] Int. Cl.² ........................................ A61B 5/04

[58] Field of Search ......... 128/2.06 E, 2.1 R, 404, 128/411, 416–418, DIG. 4, 155, 156, 163

[56] References Cited

UNITED STATES PATENTS

| 2,685,086 | 8/1954 | Henry | 128/155 X |
|---|---|---|---|
| 2,807,262 | 9/1957 | Lew | 128/156 |
| 3,092,103 | 6/1963 | Mower | 128/163 |
| 3,340,868 | 9/1967 | Darling | 128/2.06 E |
| 3,566,860 | 3/1971 | Moe, Jr. | 128/2.06 E |
| 3,587,565 | 6/1971 | Tatoian | 128/2.06 E |
| 3,701,346 | 10/1972 | Patrick, Jr. et al. | 128/2.06 E |
| 3,828,766 | 8/1974 | Krasnow | 128/2.1 E |
| 3,830,229 | 8/1974 | Johnson | 128/2.1 E |
| 3,841,312 | 10/1974 | Corasanti | 128/2.06 E |
| 3,845,757 | 11/1974 | Weyer | 128/2.1 E |
| 3,865,099 | 2/1975 | Robichaud | 128/2.06 E |
| 3,868,946 | 3/1975 | Hurley | 128/2.1 E |

Primary Examiner—Robert W. Michell
Assistant Examiner—Lee S. Cohen
Attorney, Agent, or Firm—Larson, Taylor and Hinds

[57] ABSTRACT

An electrode arrangement is presented which provides for a reliable electrical contact with the skin of a person or animal. The electrode arrangement comprises, in combination, a central post with a base flange, an adhesive pad having a central aperture for receiving the central post, a gel member and a resilient o-ring shaped member. An alternate embodiment comprises a central post and base flange, an adhesive pad having a central aperture for receiving the central post, and a shield washer, with a central aperture for receiving the central post, mounted above the adhesive pad. Both embodiments minimize the effect of physical forces placed on the electrical contact.

11 Claims, 7 Drawing Figures

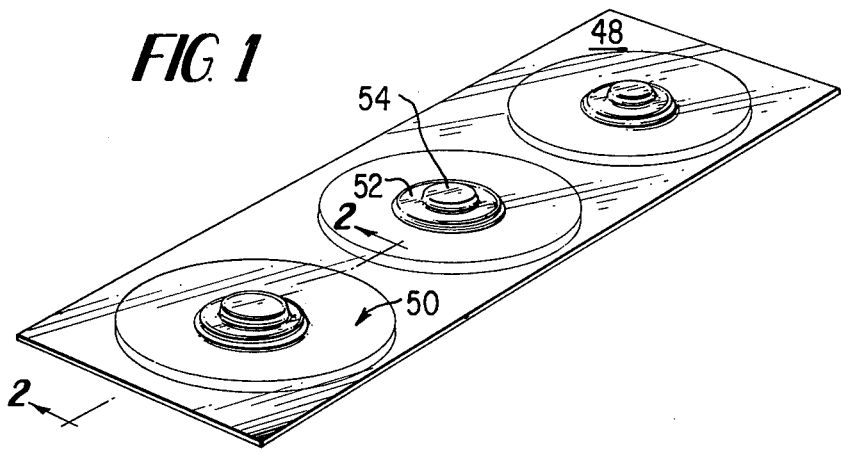
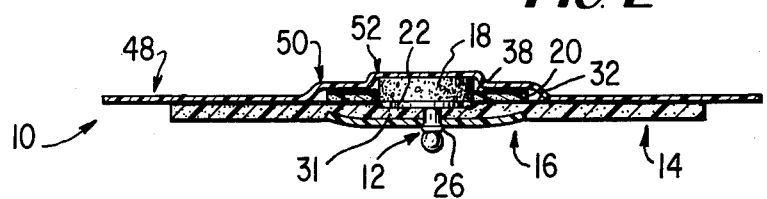
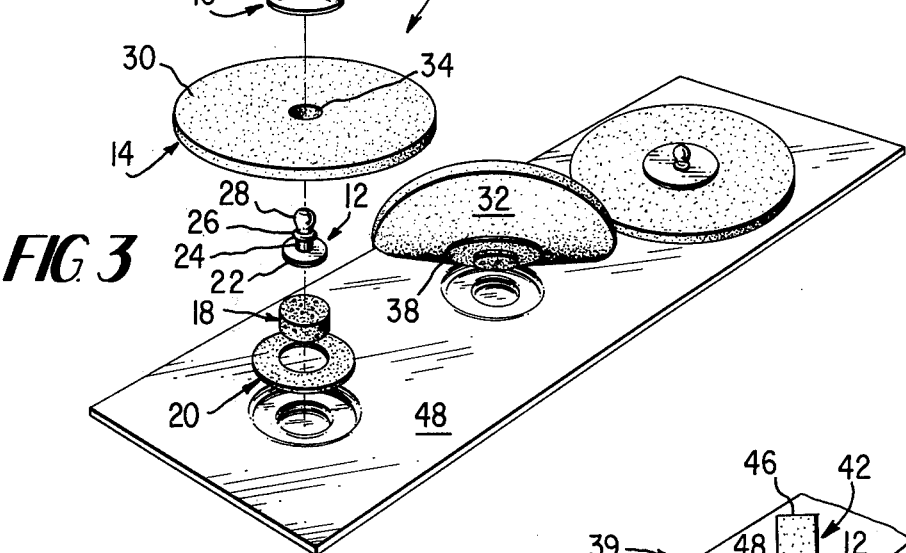
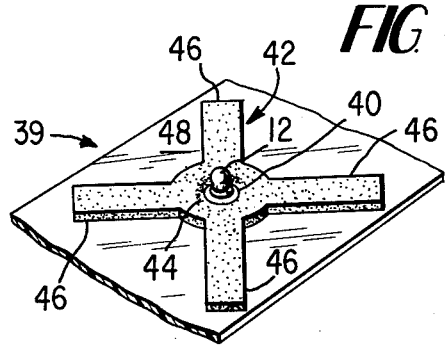

ELECTRODE ARRANGEMENT

BACKGROUND OF THE INVENTION

1. Field Of The Invention

This invention relates generally to the field of electrode arrangements and, more particularly, to the field of electrode arrangements useful for EEG and ECG systems.

2. Description Of The Prior Art

Various electrode arrangements have been developed for electrocardiogram systems which produce electrocardiograms that are accurately representative of the heart beat of a person or animal. Two such electrode arrangements are disclosed in a U.S. Pat. No. 3,841,312 to Corasanti, the inventor of the device herein described and No. 3,845,757 to Weyer. Electrodes of the type disclosed in the Corasanti patent detect electric potentials or voltages generated by a body and are electrically connected to measuring instruments where the voltages are recorded.

The body generates a minimum, relatively constant voltage, called the base line voltage, and variable wave form types of voltages, associated for example with heart beats and brain waves, superimposed on the base line voltage. A disadvantage associated with prior art electrode arrangements is that after a base line voltage is established on the measuring instruments of the EEG or ECG system, pressure or force on the electrode itself tends to cause an otherwise constant amplitude base line voltage to oscillate as a low frequency wave form. Consequently, the base line appears to shift from its original steady state amplitude. These shifts of the base line can tend to obscure the wave forms of the heart beat signal. A U.S. Pat. No. 3,518,984, issued to Mason, notes and explains in some detail the problem of baseline shift. Consequently, a need exists for a reliable, low cost, disposable electrode arrangement that can maintain a good electrical contact despite the placement of pressure or force upon the electrode.

A further disadvantage of prior art electrodes is that a sharp, instantaneous force on the electrode produces voltage wave forms which are similar to and can be mistaken for the variable, high frequency wave form types of voltages associated with, for example, heart beats.

Another disadvantage of prior art electrodes is that they are too rigid and not adaptable for placement on non-planar areas of the adult body or on limited surface areas presented by, for example, a premature or infant body.

Another disadvantage of prior art device is that they can not be removed from their package prior to use. The usefulness of existing electrodes in emergency situations could be substantially improved if existing electrodes could be removed from their packages and attached to the EEG system prior to the emergency situation. However, existing electrodes can not be removed from their packages for long periods before being used without the dehydration of the gel member and thus without greatly affecting the nature of the electrical contact.

SUMMARY OF THE INVENTION

The present invention provides for an electrode arrangement that overcomes the problems of baseline shift, false heart beat wave forms, poor adaption to various bodily contours, and dehydration of the gel member.

In accordance with an aspect of the invention, an electrode arrangement for use as electrical contact with the skin of a person or animal is provided which comprises an electrode having a central post with a base flange, an adhesive pad having a central aperture for receiving the central post of the electrode, a gel member that covers the bottom surface of the base flange of the electrode and retaining member for retaining the electrode and adhesive pad together, the retaining member also serving as a shield mechanism for protecting the gel member from pressure or force placed on the electrode.

Another aspect of the invention provides for an O-ring for circumscribing and protecting the gel member from migration from its position directly beneath the base flange of the electrode.

A further aspect of the invention provides for a preserving mechanism for preventing the gel member from becoming dehydrated. Additional features and advantages of the invention will be set forth in, or apparent from the detailed description of preferred embodiments of the invention found hereinbelow.

BRIEF DESCRIPTION OF THE DRAWINGS

FIG. 1 is a perspective view from the bottom of three electrode arrangements mounted on a preserving backing in accord with one embodiment of the invention;

FIG. 2 is an elevational sectional view taken along line 2—2 of FIG. 1;

FIG. 3 is an exploded view in perspective of the electrode arrangement as shown in FIG. 2;

FIG. 4 is a perspective view of an electrode arrangement in accordance with a further embodiment of the invention;

DETAILED DESCRIPTION OF THE PREFERRED EMBODIMENTS

Figure 5:
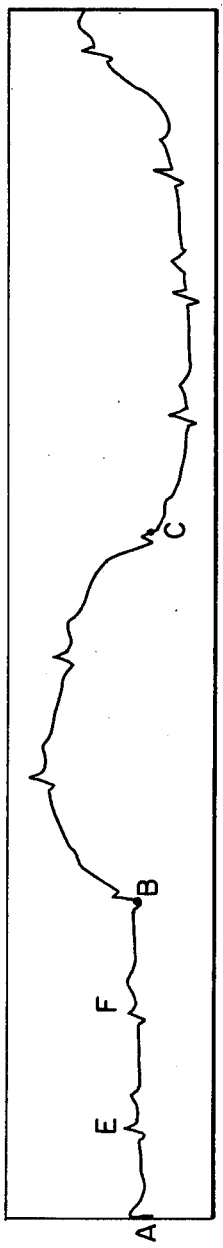
FIG. 5 is a graph depicting the measurements of an EEG or ECG system which uses a prior art electrode.

Referring to the drawings, and, in particular to FIGS. 2 and 3, an electrode arrangement in accordance with the invention is presented and generally denoted 10. As can best be seen in the exploded view in FIG. 3, electrode arrangement 10 comprises a stud 12 and the following elements in coaxial orientation thereto: a circular washer 16, an adhesive pad 14, a gel member 18, and an O-ring 20.

Stud 12 comprises a circular base flange 22, an upstanding post 24 integrally mounted on flange 22 and coaxial therewith, a spherical knob 28 which caps post 24 and is integral therewith, and flange 26, circumscribing post 24 between knob 28 and base flange 22.

Stud 12 is preferably comprised of a plastic material with a silver coating adhering to the entire outer surface of the plastic material. However, stud 12 may comprise a solid one piece structure depicted in FIG. 3, or it may comprise a plurality of pieces that snap or fit together. Further, it should be understood that stud 12 may be comprised of or coated with any combination of materials which affords it electrical conductivity qualities.

Adhesive pad 14 is preferably comprised of only insulative materials and includes a disc-shaped pad 30, an adhesive layer 32 covering the bottom of pad 30, and a central aperture 34. Pad 30 preferably is comprised of a soft, compliant but tough foam material.

Washer 16 is circular in shape and has a central aperture 36. Preferably washer 16 is dome shaped and is comprised of a tough and rigid material such as nylon. The diameter of washer 16 is equal to or larger than the diameter of O-ring 20. The gel member 18 preferably comprises an open-cellular sponge material impregnated with an electrically conductive gel. It is possible, however, to replace gel member 18 with an electrically conductive gel compound that can be applied either to the electrode 10 while electrode 10 is being assembled or just prior to the placement of electrode 10 on a patient's skin, or to the patient's skin directly. The O-ring 20 comprises a somewhat compliant foam material and may have an adhesive layer 38.

With reference to FIG. 2 and FIG. 3, stud 12 fits into central aperture 34 of adhesive pad 14 such that base flange 22 contacts and adheres to adhesive layer 32, and post 24 extends through central aperture 34, so that post flange 26 is located above (see FIG. 3) adhesive pad 14. Washer 16 is forced downwardly over knob 28 and flange 26 so that adhesive pad 14 is firmly retained between the base flange 22 and the washer 16. When electrode arrangement 10 is assembled, the portion 31 of adhesive pad 14 (see FIG. 2) between base flange 22 and washer 16 is slightly compressed such that base flange 22 is recessed (see FIG. 2) into adhesive pad 14.

The gel member 18 covers the bottom surface of base flange 22 of stud 12 and may extend beyond the outer periphery of base flange 22. Gel member 18 may be maintained in contact with base flange 22 by adherence of the outer peripheral portions of the gel member to adhesive pad 14. A gel member 18 which does not have outer peripheral portions and which is equal to or smaller in diameter than base flange 22 of stud 12, may be maintained in contact with base flange 22 by static or hydraulic pressure. O-ring 20 adheres to adhesive layer 32 of adhesive pad 14 and circumscribes gel member 18.

Electrode 10 further comprises a preserving backing 48 to which the adhesive pad 14 is removably mounted (see FIGS. 1 and 2). Preserving backing 48 is preferably made of a polyester material such as Mylar (polyethylene terephthalate) or any of a variety of moisture retaining materials. Backing 48 includes a plurality of recesses 50 impressed therein. Recesses 50 are defined by an annular shallow portion 52 and a central deeper disc-shaped portion 54. Adhesive layer 38 of O-ring 20 adheres to the surface of recesses 50. Disc-shaped portion 54 of the plurality of recesses 50 encloses but does not deform gel member 18.

In use, preserving backing 48 is removed from electrode arrangement 10 and arrangement 10 is placed on the body of a person or an animal at the point where a reliable electrical contact is desired. Such a contact would be necessary, if for example, a heart beat signal is to be measured. The adhesive layers 32 and 38 hold the electrode arrangement 10 in contact with the body.

An electrically conductive path is maintained from the body surface of the person through electrically conductive gel member 18 and electrically conductive stud 12 to electrically conductive leads (not shown) attachable to knob 28 of stud 12. The leads electrically connect electrode arrangement 10 to an EEG or ECG system. Since the skin does not usually transmit signals along the length thereof, and since only gel member 18, and not adhesive pad 14 is conductive, generally only voltage signals that originate beneath gel member 18 are transmitted through stud 12 to the ECG system.

The voltage signals sensed by electrode 10 generally fall into two classifications: those that represent the patient's heart beat, and those that are extraneous, being caused by vertical or horizontal force placed on electrode 10 or on the patient's skin. It is desirable to eliminate the voltage signal caused by these forces since they generally appear either as base line shifts or false heart beat signals on a recording of a signal. The base line is a reference line caused by a minimum relatively constant body voltage from which the magnitude of superimposed wave form voltage signals caused by, for example, heart beats, are measured.

FIG. 5 represents the recording of an electrical signal by an EEG or ECG system which comprises a prior art electrode. The section of the graph generally depicted between points A and B represent a base line with two measured signals, for example, heart beat signals, superimposed on the base line at points E and F. The section of the graph generally depicted between points B and C represents a base line which has been shifted upward from the base line established between points A and B. The shift in the base line probably occured when a force was applied to the electrode arrangement being used. The frequencies contained in the pressure caused base line shift are usually very low in comparison to the frequencies contained in the heart beat signals. As can be seen at point B, the forces which cause the base line shift also distort the heart beat signals.

Further, if quick, sharp forces are inflicted on the skin, a narrow signal of a high frequency (not shown) is created that could erroneously be interpreted as a heart beat signal. Thus, in order to prevent extraneous signals and since even small areas of skin generate sizable voltage signals when exposed to these forces, it is necessary to isolate the skin under gel member 18 and the gel member 18 from these forces.

Isolation of the skin from vertical forces is accomplished by adhesive pad 14, washer 16, O-ring 20, and the recession of stud 12 into adhesive pad 14. Since adhesive pad 14 is composed of a thick, compliant but tough foam, it can absorb the vertical forces and thereby also reduce patient discomfort that would occur if force were applied to a less compliant material. Further between the flange 22 of stud 12 and the skin is a gel member 18 of a soft compressible foam which insulates the skin thereunder from forces on electrode 10. Also stud 12, being recessed into adhesive pad 14, is held further away from the skin than if base 22 were placed flush with layer 32. Consequently, the placement of stud 12 further isolates the skin from forces on electrode 10. Washer 16 acts as a shield and transmits vertical forces through adhesive pad 14 and O-ring 20 to the annular skin outside of the circular skin area covered by gel member 18.

Isolation of gel pad 18 from lateral stretching forces is also accomplished by the tough foam of adhesive pad 14 which absorbs these forces without allowing the skin under gel pad 18 to become stretched.

Figure 6:
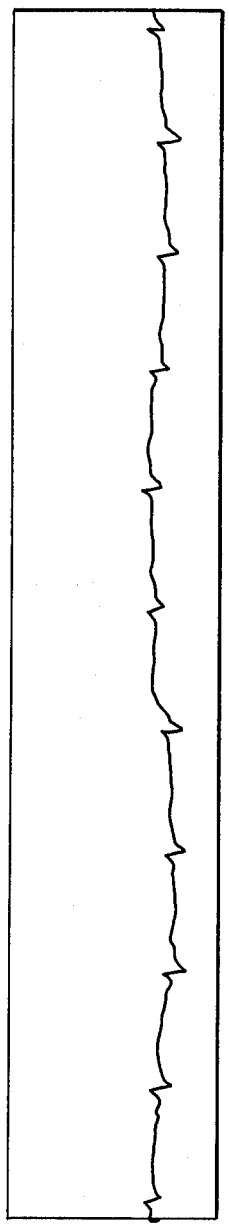
FIG. 6 is a graph depicting the measurements of an EEG or ECG system which uses an electrode with an embodiment as depicted in FIG. 3.

FIG. 6 represents the recording of a signal with an EEG or ECG system using an electrode arrangement 10 such as that depicted in FIG. 3 with a shield washer 16 and an O-ring 20. Even though a force capable of producing a base line shift as depicted by the portion of the graph in FIG. 5 generally between points B and C was applied to the preferred arrangement 10, no appreciable base line shift was recorded on the graph in FIG. 6.

There are additional advantages associated with the use of O-ring 20. O-ring 20 confines gel member 18 and prevents migration of conductive gel therefrom. O-ring 20 also adds flexibility to the electrode arrangement 10 in that arrangement 10 is more easily adaptable to a bony area of the body. Even though adhesive pad 14 is compliant, it will not conform easily to non-planar surfaces. However, O-ring 20 allows electrode 10 to be placed on non-planar surfaces of the skin without loss of the electrical contact.

An additional advantage of the added flexibility which O-ring 20 enables electrode arrangement 10 to have, is that since electrode arrangement 10 conforms quite closely to the skin, gel member 18 is completely contained in an air tight seal defined by the skin, adhesive pad 14, and O-ring 20, and thus prevented from dehydrating.

Aside from protecting electrode from forces while in use, it has been found necessary to protect electrode 10, and especially gel member 18, while electrode 10 is being stored. Thus, preserving strip 48 is used to protect electrode 10. Preserving strip 48 completely enclosed the exposed portion of gel member 18 and thus prevents any movement of the conductive gel from gel member 18 and also prevents dehydration of gel member 18. Consequently, in an emergency room situation, a plurality of electrode arrangements 10 can be removed from their package (not shown) and made ready for immediate use. The electrode arrangement 10 can be left mounted on strip 48 and at the same time be connected to an EEG system by leads (not shown). The unpackaged electrode arrangement 10 will thus be instantly ready for an emergency and the gel member 18 will be protected from dehydration for a period of days.

Figure 7:
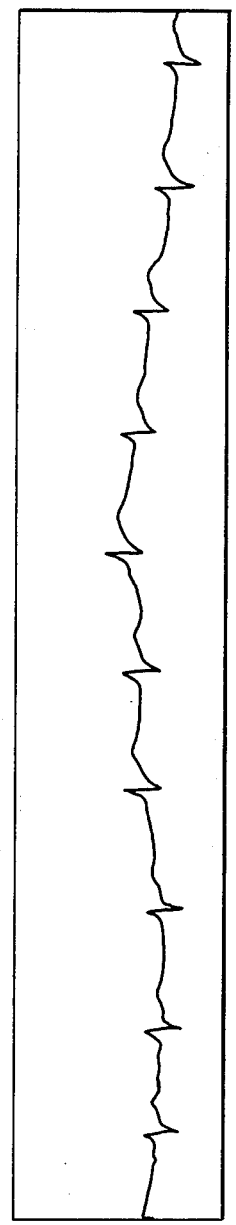
FIG. 7 is a graph depicting the measurements of an EEG or ECG system which uses an electrode in accordance with a further aspect of the invention as depicted in FIG. 3.

It should be understood that an alternate embodiment of electrode arrangement 10 (FIG. 3) can exclude shielding washer 16, and substitute therefor a retaining ring which is smaller in size than washer 16 for mechanically securing the stud to the adhesive pad. One such embodiment when incorporated into an EEG or ECG system produces a graph of the measured signal as represented in FIG. 7. Even though a force capable of producing a base line shift was applied to the embodiment, no appreciable base line shift appeared on the graph.

It should also be understood that the electrode arrangement 10 does not require either a retaining ring or the shield and furthermore post flange 26 of stud 12 can be eliminated. In such an embodiment as in the embodiment in FIG. 3, the upper surface of base flange 22 of stud 12 adheres to adhesive layer 32 of adhesive pad 14. Also post 24 of stud 12 is forced through central aperture 34 of adhesive pad 14 and held in aperture 34 by friction. Consequently, stud 12 can be held on pad 14 without the use of any combination of a shielding washer such as washer 16 (FIG. 3), a retaining ring, and a post flange such as flange 26 (FIG. 3).

In specific instances, it is preferable to avoid the rigidity of shielding washer 16 and adhesive pad 14, but retain some form of adhesive member and retaining member by which stud 12 is secured to the adhesive member other than just by adhesive and frictional means as described above. Such instances arise more frequently as the size of the person or animal to be tested decreases since smaller more curved surface areas must be accommodated. Thus, the alternate embodiment as depicted in FIG. 4 is more suitable for smaller bodies and in particular premature babies. Electrode arrangement 39, (FIG. 4) depicts an electrode without a shielding washer. A retaining ring 40 mechanically secures stud 12 to adhesive pad 42. Adhesive pad 42 (FIG. 4) is thinner and more flexible than adhesive pad 14 (FIG. 3). Furthermore, pad 42 is comprised of a central disc 44 and a plurality of appendages 46. In a preferred embodiment, the length of appendages 46 are at least as long as the diameter of central disc 44. Appendages 46 permit the electrode arrangement to be securely attached to skin surfaces of small diameters, such as the arms and legs of premature babies. The embodiment 39 depicted in FIG. 4 can comprise an O-ring (not shown) and a gel member (not shown) similar to O-ring 20 and gel member 18 of FIG. 3.

A further embodiment (not shown) of an electrode arrangement which can be used in very confined areas of a body is similar in construction to electrode arrangement 39 depicted in FIG. 4. In this embodiment, adhesive pad 42 of electrode 39 in FIG. 4 is replaced by an adhesive pad which is comprised of only a central disc similar in shape and size to central disc 44 of FIG. 4. Such an embodiment can also comprise an O-ring and a gel member to O-ring 20 and gel member 18 of FIG. 3.

Although the present invention has been described relative to exemplary embodiments thereof, it will be understood by those skilled in the art that variations and modifications can be effected in these embodiments without departing from the scope and spirit of the invention.

I claim:

1. An electrode arrangement for making an electrical contact with the skin of the body of a patient comprising, in combination:

an electrode element including a base flange with upper and lower surfaces and a central post upstanding from said upper surface, said electrode element being conductive;

a flexible adhesive pad for adhering to the body, said adhesive pad including a foam pad member having upper and lower surfaces and an adhesive layer provided on, and coextensive with, said lower surface of said foam pad member, said adhesive pad having a central aperture received by said central post, said central post extending through said central aperture such that a portion of said central post extends above said upper surface of said adhesive pad, said upper surface of said base flange disposed adjacent to, and adhering to, said adhesive layer, said adhesive pad extending beyond the periphery of said base flange a flexible, foam, O-ring-shaped member adhering to said adhesive layer of said adhesive pad such that said O-ring-shaped member circumscribes said base flange of said electrode element; and a shielding means comprising a dome-shaped annular washer, comprised of a tough, rigid material, received by said central post adjacent said upper surface of said adhesive pad, said shielding means for shielding said base flange from forces to which said electrode arrangement can be exposed, said annular washer having an outside diameter generally equivalent to the outside diameter of said O-ring-shaped member for deflecting the forces away from said base flange to said O-ring-shaped member without decreasing the flexibility and the ability of said adhesive pad to conform to the body of a patient.

2. An electrode arrangement in accordance with claim 1 further including a gel means covering said lower surface of said base flange, said gel means circumscribed by said O-ring-shaped member.

3. An electrode arrangement in accordance with claim 2 wherein said gel means includes a cylindrically-shaped foam pad impregnated with a conductive gel substance.

4. An electrode arrangement in accordance with claim 3 wherein said gel means extends outwardly beyond the outer periphery of said base flange, said gel means being maintained in contact with said base flange by adherence between the outer peripheral portions of said gel means and said adhesive layer of said adhesive pad.

5. An electrode arrangement in accordance with claim 3 wherein said gel means extends outwardly from said adhesive layer farther than said O-ring-shaped member extends.

6. An electrode arrangement in accordance with claim 5 wherein said O-ring-shaped member has a lower exposed surface that is parallel to said adhesive pad, said exposed surface having an adhesive layer affixed thereto.

7. An electrode arrangement in accordance with claim 6 further comprising a preserving means for preventing said gel means from dehydrating, said preserving means being removably secured to said adhesive pad of said electrode arrangement and including a plurality of recesses which comprise an annular shallow portion and a central, coaxially-located, deeper disc-shaped portion, said adhesive layer of said O-ring-shaped member adhering to said annular shallow portion, and said gel means protectively received without being deformed by said deeper, disc-shaped portion.

8. An electrode arrangement in accordance with claim 7 wherein said preserving means comprises a firm, non-metallic, non-conductive member for protecting said gel means from mechanical forces.

9. An electrode arrangement in accordance with claim 1 wherein said central post comprises a knob-shaped portion located distally from said base flange to provide means for connecting said central post with an electrode connector.

10. An electrode arrangement in accordance with claim 1 wherein said electrode element is of integral, one piece, and solid construction.

11. An electrode arrangement in accordance with claim 1 wherein said adhesive pad includes a plurality of appendages extending radially therefrom.

* * * * *